United States Patent
Yamamoto

(10) Patent No.: US 7,037,107 B2
(45) Date of Patent: May 2, 2006

(54) ORTHODONTIC ARCHWIRE, ARCHWIRE ELEMENTS AND WIRE CUTTING TOOL

(76) Inventor: Saburo Yamamoto, 27-5 Gotenyama 4-chome, Takarazuka-shi Hyogo-ken (JP) 665-0841

( * ) Notice: Subject to any disclaimer, the term of this patent is extended or adjusted under 35 U.S.C. 154(b) by 253 days.

(21) Appl. No.: 10/251,488

(22) Filed: Sep. 18, 2002

(65) Prior Publication Data

US 2003/0073052 A1    Apr. 17, 2003

(30) Foreign Application Priority Data

Oct. 12, 2001    (JP)    ............... 2001-314865

(51) Int. Cl.
*A61C 3/00*    (2006.01)
(52) U.S. Cl. ...................................................... 433/20
(58) Field of Classification Search ................. 433/20, 433/17, 22
See application file for complete search history.

(56) References Cited

U.S. PATENT DOCUMENTS

| 1,938,428 | A | * | 12/1933 | Johnson ....................... 433/20 |
| 4,412,819 | A |   | 11/1983 | Cannon |
| 4,424,031 | A | * | 1/1984  | Dahan .......................... 433/18 |
| 4,815,968 | A | * | 3/1989  | Keller ............................ 433/7 |
| 5,816,800 | A | * | 10/1998 | Brehm et al. .................. 433/7 |

FOREIGN PATENT DOCUMENTS

JP    6-34607    5/1994

* cited by examiner

*Primary Examiner*—John J Wilson

(57) ABSTRACT

The posterior segment 20 of the orthodontic archwire of the present invention has the connector 30 provided in advance on the free end 23 of a loop 22 formed by bending one end of the segment. The archwire 1 where the main wire portion 10 of the anterior segment 10 is connected to the main wire portion 21 of the posterior segment 20 on the same axial center can be obtained by inserting and securing the connection end 12 formed by bending each opposite end of the said anterior segment 10 into the said connector 30.

2 Claims, 11 Drawing Sheets

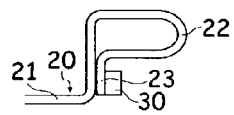
FIG.13
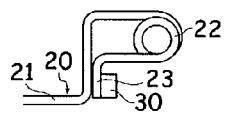
FIG.14
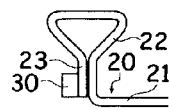
FIG.15
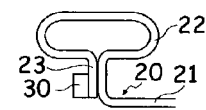
FIG.16
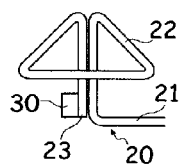
FIG.17
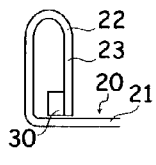
FIG.18
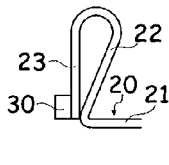
FIG.19
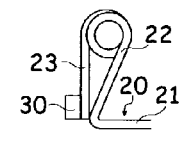
FIG.20
FIG.21
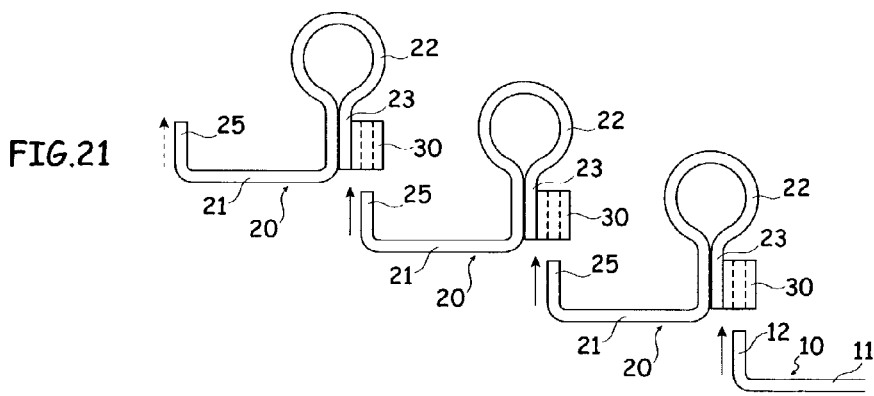
FIG.22
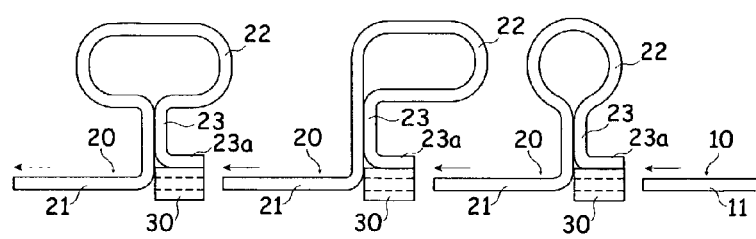

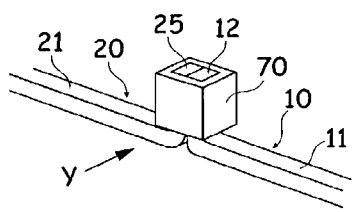 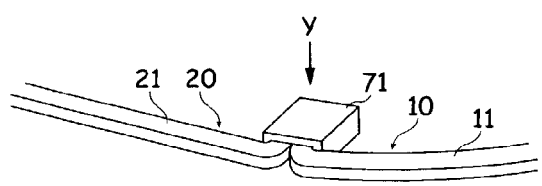
FIG.61     FIG.62
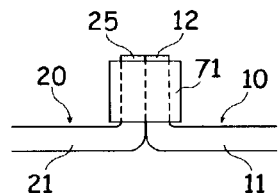
FIG.63
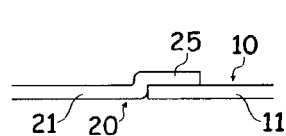 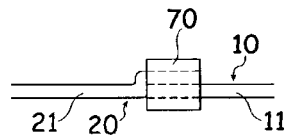
FIG.64     FIG.65
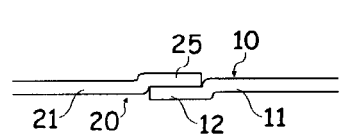 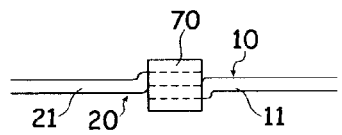
FIG.66     FIG.67
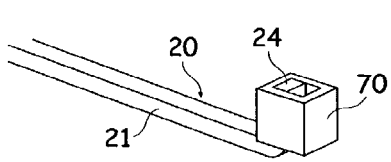 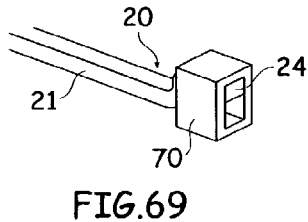
FIG.68     FIG.69
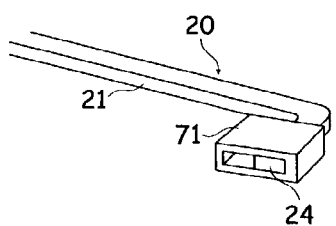
FIG.70

ORTHODONTIC ARCHWIRE, ARCHWIRE ELEMENTS AND WIRE CUTTING TOOL

BACKGROUND OF THE INVENTION

This invention relates to the archwire for orthodontics especially the archwire for orthodontics which consists of two or more wire components and a wire component. It is also related with the wire cutting tool used for cutting of the said wire component.

It is a principle that the main wire portions of the orthodontic archwire are on the same plane and the same axial center irrespective of the presence of loops. The main wire portion of the orthodontic archwire points to a portion without curvature, such as a loop in the orthodontic archwire here.

It was difficult and skillful work to bend two or more loops in the same form by hand using one wire component. It was also difficult and skillful work to make an orthodontic archwire with some loops according to the above-mentioned principle. Consequently, producing an orthodontic archwire with some loops needed long treatment times. A wire which was longer than the dental arch length of the patient was tried into the patient's mouth at the time of measurement, with the end of the wire pressed against the patient's oral mucosa. During this procedure the patient was in pain.

The preformed archwire with loops settled the above-mentioned faults. However, when treating orthodontics using a preformed archwire with loops, a variety of preformed archwires with different loop spacings, loop forms, etc. needed to be arranged, and inventory control was complicated as well. Moreover, a preformed archwire with loops was not used when the distance between loops was outside regulations. Furthermore, the preformed archwire with loops was not used, when the positions where loops would be placed were bilaterally asymmetrical, since the loops were arranged in symmetry. Moreover, since it was necessary to combine a setup of each distance between loops in order to obtain an archwire with loops of a large number like multi-loop edgewise archwire with the ready-made article, there was a problem that exceeding great numbers of wires had to be prepared. Thus, in the flexibility of a design of an archwire, and in the simplicity of stock management of an archwire, the preformed archwire was inferior in the case where the archwire was hand made.

On the other hand, the method which connects two or more wire components with a connector, produces the archwire for orthodontics as indicated by the U.S. Pat. No. 4,412,819 and the Japanese patent No. 6-34607.

In a composite orthodontic archwire according to the U.S. Pat. No. 4,412,819, the wire of an anterior segment 50 and the wires of posterior segments 51, 51 are connected with the connectors 52, 52 (FIG. 71). Since the ends of these two wires have overlapped in this connection structure, there was a misalignment in the axial center of these two wires 50, 51 (FIG. 72).

On the other hand, in a composite orthodontic archwire according to the Japanese patent No. 6-34607, the wire of the anterior segment 60 and the wires of the posterior segments 61, 61 are connected with the connectors 62, 62 (FIG. 73). Respective ends of these wires 60, 61 were connected by grips 62a, 62b of the connectors and arranged to the upper and lower sides or right and left (FIGS. 74 and 75). However, even if it was this connection structure, these two wires 60, 61 could not be connected with the same axial center, so there is a level difference.

Since a level difference arises between the axial centers of these wires, the connection structure of these wires does not meet the above-mentioned principle for the orthodontic archwire. For this reason, in using the archwires produced by these methods, in order to correct the misalignment of the axial center of the wires, the brackets and the archwires needed for adjustment, and this adjustment work was complicated.

Japanese patent 6-34607 also shows the connection structure without a level difference between axial centers of the wires (FIG. 76). However, since grips 62a, 62b for securing a wire were arranged in series, the size of the direction of an axial center of a connector is long. Therefore, when the distance between brackets was short, this connector was not used.

Moreover, with this technology, the connector needed to be simultaneously supported with respective wires at the time of connection, connection was not easy and positioning accuracy was bad.

BRIEF SUMMARY OF THE INVENTION

In view of the above problems, it is an object of the present invention to provide an orthodontic wire element and wire cutting tool which allow easy connection of multiple wire elements, offers a wide range of applications, provides easy inventory control, alleviates patients' pain in the manufacture of archwires, and makes it possible to fabricate archwires with loops in an easy way, as well as to provide an orthodontic archwire with a wide range of applications that connects multiple wire elements on the same axial center.

The archwire elements of the present invention are provided with a wire connector in advance at one end of the wire in such a way that the axial center of the main wire portion agrees with the axial center of the connector. In the case where archwire elements are provided with loops, the wire connector is provided in advance on the leg at the free end of each loop in such a way that the axial center of the main wire portion and the axial center of the connector are aligned with each other. The main wire portions of two wires are arranged on the same axial center and connected to each other by inserting and securing one end of a wire into the connector of the wire element with connector. A composite archwire in which the main wire portions of anterior and posterior segments are arranged on the same axial center can be created by connecting the said wire element with connector, or the posterior segment, to each of the opposite ends of a generally U-shaped archwire, or the anterior segment.

Another type archwire element of the present invention is provided with a wire connector at one end of the wire in such a way that the axial center of the main wire portion crosses at right angles with the axial center of the connector. In the case of archwire elements provided with loops, the wire connector is provided in advance on the leg at the free end of each loop in such a way that the axial center of the main wire portion and the axial center of the connector cross at right angles. The main wire portions of the two wires are arranged on the same axial center and connected to each other by inserting and securing the connection end formed by bending one end of a wire, into the connector of the wire element with connector. A composite archwire in which the main wire portions of anterior and posterior segments are arranged on the same axial center can be created by connecting the said wire element, or the posterior segment, to the generally U-shaped archwire, or the anterior segment, at each of the connection ends formed by bending the opposite ends.

The wire cutting tool of the present invention has a design in which the bottom surface of the cutting edge formed on the left cutting die has the same shape as the bottom surface of the cutting edge receiver formed on the right cutting die, and both the said cutting edge and the cutting edge receiver has almost the same height as the connection end formed by the wire which is to be connected to the wire element with connector. The use of this wire cutting tool makes it possible to cut the connection end easily to a desirable height when fabricating a connection end on the mating wire to be inserted into the connector.

The archwire consisting of multiple wire elements of the present invention joins wire elements at the connection ends formed by bending one end of each wire element. This design makes it possible to create a composite archwire in which the main wire portions of the two segments are arranged on the same axial center.

An example of the wire cutting tool of the present invention (perspective view)

FIGS. 59, 60

Figure 58:
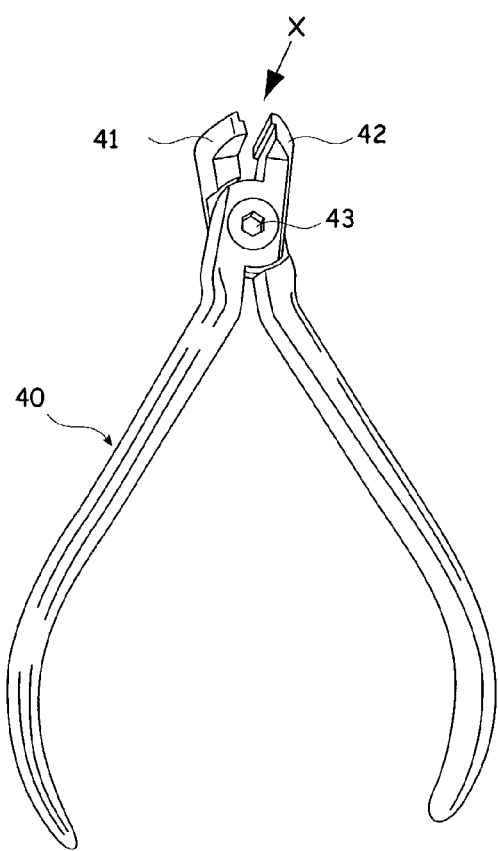
FIG. 58
Figure 59:
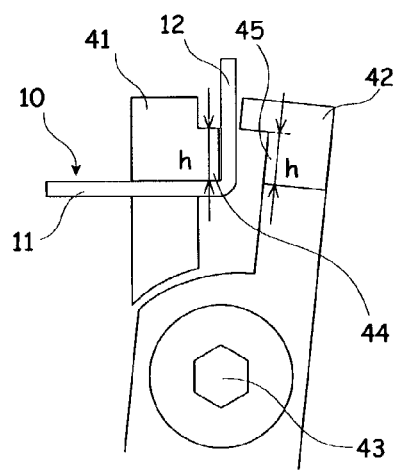
Figure 60:
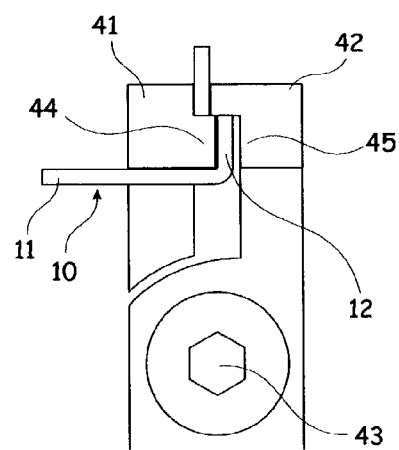

Partially enlarged views of the wire cutting tool viewed from the arrow X in FIG. 58 (FIG. 59: before cutting of a wire element, FIG. 60: after cutting of a wire element)

FIGS. 61, 62

An example of an archwire consisting of multiple wire elements of the present invention (perspective views)

FIG. 63

A view looking from the arrow Y in FIGS. 61 and 62

FIGS. 64, 65

Another example of the join of an archwire consisting of multiple wire elements of the present invention (FIG. 64: before joining, FIG. 65: after joining)

FIGS. 66, 67

Another example of the join of an archwire consisting of multiple wire elements of the present invention (FIG. 66: before joining, FIG. 67: after joining)

FIG. 68

Another modification of the fourth embodiment of the present invention (perspective view)

FIG. 69

Another modification of the fifth embodiment of the present invention (perspective view)

FIG. 70

Another modification of the ninth embodiment of the present invention (perspective view)

FIG. 71

A conventional art 1 of an archwire composed of multiple wires

FIG. 72

Figure 71:
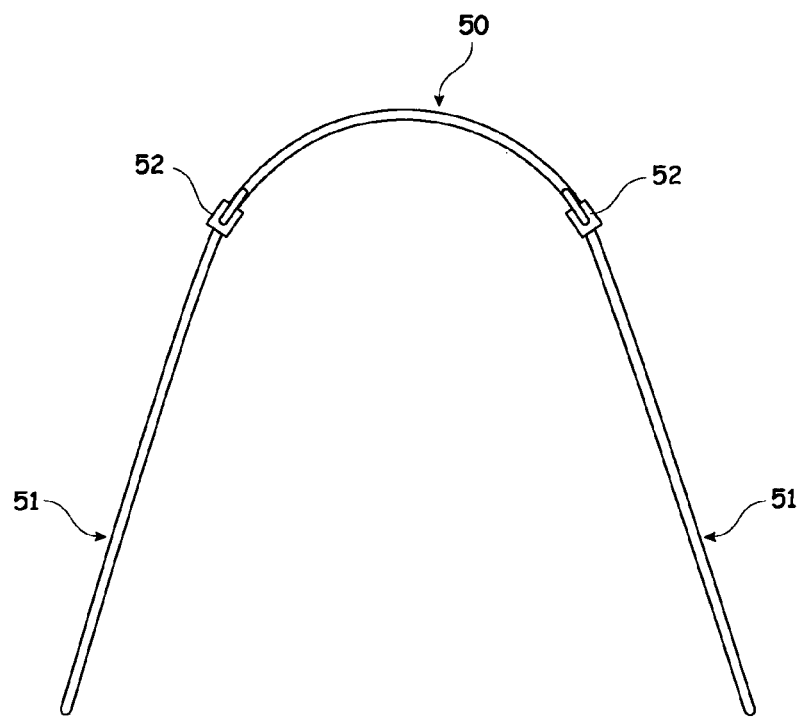
Figure 72:
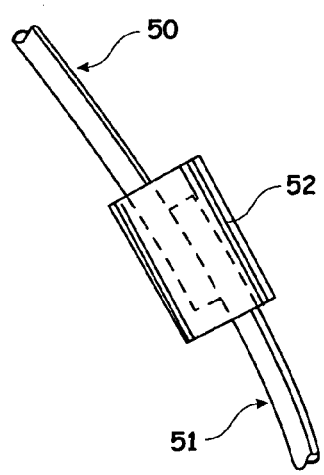

An enlarged view of the connection in FIG. 71

FIG. 73

A conventional art 2 of an archwire composed of multiple wires

FIGS. 74, 75, 76

Figure 73:
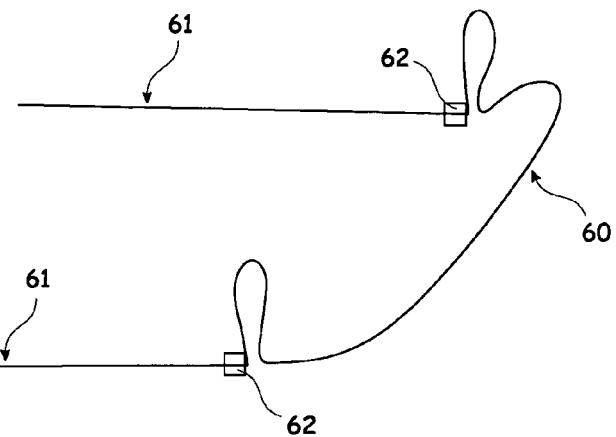
Figure 74:
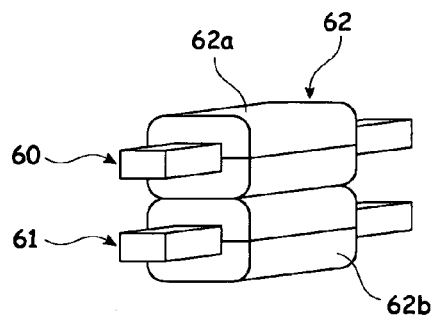
Figure 75:
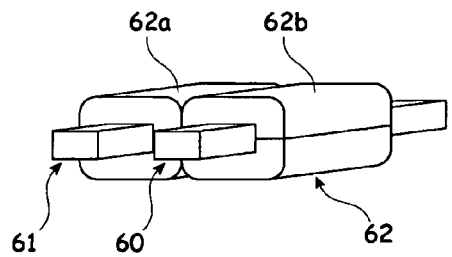
Figure 76:
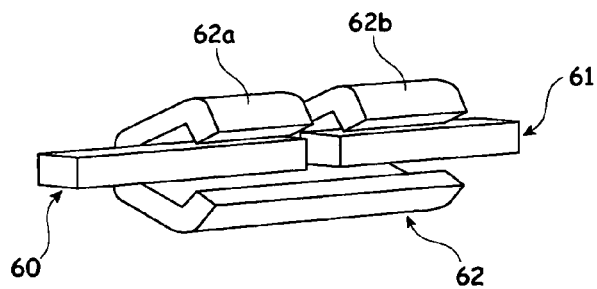

Examples of the connection in FIG. 73

DETAILED DESCRIPTION OF THE INVENTION

Figure 1:
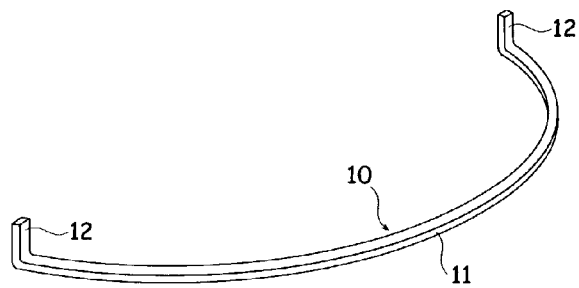
FIG. 1
The first embodiment of the present invention (perspective view)
FIG. 2
The second embodiment of the present invention (perspective view)
FIGS. 3, 4
Overall perspective views of the method of connecting the first and second embodiments of the present invention (FIG. 3: before assembly, FIG. 4: after assembly)
FIGS. 5, 6
Enlarged perspective views of the join achieved by using the connection methods described in the first and second embodiments of the present invention (FIG. 7: before assembly, FIG. 8: after assembly)
FIGS. 7, 8
Enlarged side views of the join achieved by using the connection methods described in the first and second embodiments of the present invention (FIG. 7: before assembly, FIG. 8: after assembly)
FIG. 9
The third embodiment of the present invention (perspective view)
FIG. 10
The connection method described in the third embodiment of the present invention (side view)
FIGS. 11, 12
Modifications of the third embodiment of the present invention (side views)
FIGS. 13, 14, 15, 16, 17, 18, 19, 20
Modifications of the loop formed on the posterior segment (side views)
FIG. 21
An application of the second embodiment of the present invention into a multiple-loop wire (side view)
FIG. 22
An application of the third embodiment of the present invention into a multiple-loop wire (side view)
FIG. 23
The fourth embodiment of the present invention (perspective view)
FIG. 24
The connection method described in the fourth embodiment of the present invention (side view)
FIGS. 25, 26
Modifications of the fourth embodiment of the present invention (side views)
FIG. 27
The fifth embodiment of the present invention (perspective view)
FIG. 28
The connection method described in the fifth embodiment of the present invention (side view)
FIGS. 29, 30
Modifications of the fifth embodiment of the present invention (side views)
FIG. 31
The sixth embodiment of the present invention (perspective view)
FIG. 32
The connection method described in the sixth and second embodiments of the present invention (perspective view)
FIG. 33
The seventh embodiment of the present invention (perspective view)
FIG. 34
The eighth embodiment of the present invention (perspective view)
FIG. 35
The ninth embodiment of the present invention (perspective view)
FIG. 36
The connection method described in the seventh and eighth embodiments of the present invention (perspective view)
FIGS. 37, 38, 39, 40, 41, 42
Modifications of the connector provided on the posterior segment (perspective views)
FIG. 43
Connector with fitting projection (perspective view)
FIG. 44
An application of the connector with fitting projection (perspective view)
FIG. 45
A modification 1 of the connector with fitting projection (perspective view)
FIG. 46
An application of modification 1 of the connector with fitting projection (perspective view)
FIGS. 47, 48
Modifications 2 of the connector with fitting projection (perspective views)
FIGS. 49, 50, 51
Applications of modifications 2 of the connector with fitting projection (side views)
FIGS. 52, 53
Modifications 3 of the connector with fitting projection (perspective view)
FIG. 54
An application of modification 3 of the connector with fitting projection (side view)
FIGS. 55, 56
Modifications 4 of the connector with fitting projection (perspective views)
FIG. 57
An application of modifications 4 of the connector with fitting projection (side view)
Figure 2:
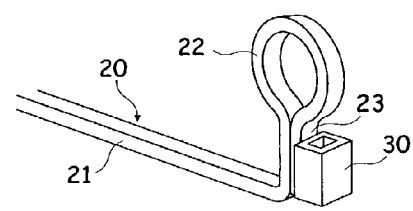
Figure 3:
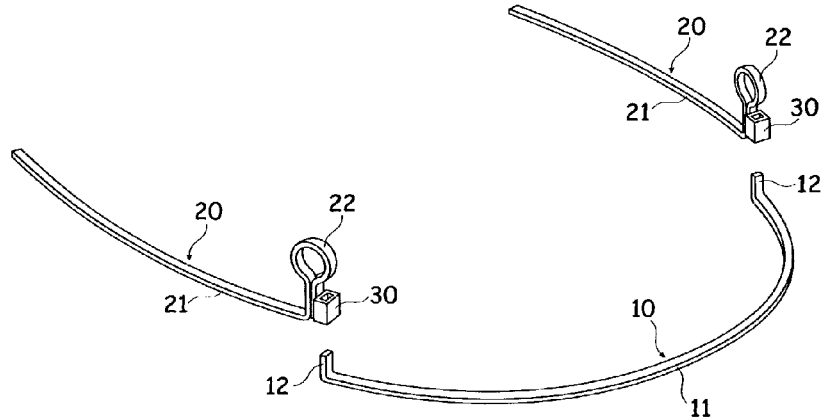
Figure 4:
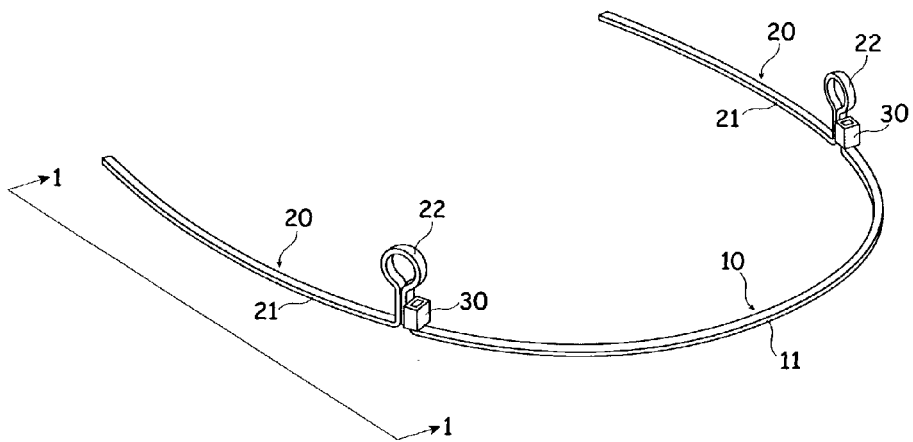
Figure 5:
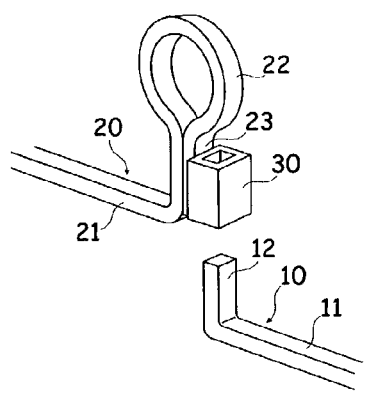
Figure 6:
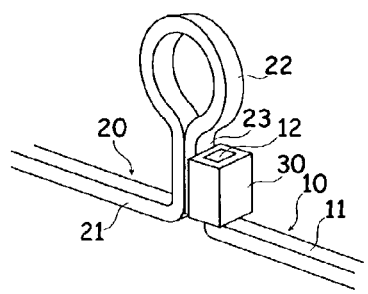

FIG. 1 shows the first embodiment of the present invention. FIG. 2 shows the second embodiment of the present invention. When the archwire 1 shown in FIG. 4 is prepared using these wire elements, the first embodiment constitutes the anterior segment of the archwire and the second embodiment forms the posterior segment (FIG. 3).

Figure 7:
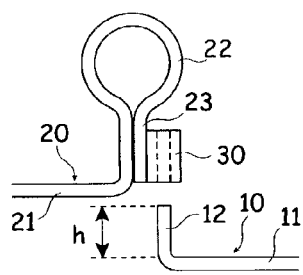
Figure 8:
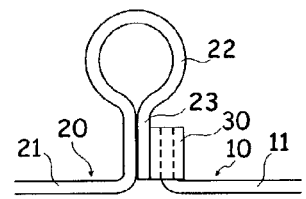

The anterior segment 10 of the first embodiment is a wire element with connection ends 12 formed by bending the opposite ends of the arched main wire portion 11 at a right angle (FIG. 1). The connection end 12 described before has a height (h) that is enough to allow it to go and get locked into the connector 30 of the posterior segment described later (FIG. 7).

The posterior segment 20 of the second embodiment is a wire element which has a loop 22 formed at one end of the straight main wire portion and the connector 30 provided in advance at the free end 23 on the leg of the loop 22 (FIG. 2). This connector 30 is provided to the free end 23 of the loop 22 in such a way that the main wire portions (11, 21) of the two segments are positioned on the same axial center simply by inserting the connection end 12 of the said anterior segment 10 into the these connectors 30.

Therefore, as shown in FIGS. 5 to 8, the main wire portions 11, 21 of the anterior segment 10 and the posterior segment 20 are connected on the same axial center by inserting and positioning the connection end 12 of the anterior segment 10 from downward into the connector 30 of the posterior segment 20 and then by crimping the above connector 30 with pliers. That is, an archwire with loops 1 as shown in FIG. 4 can be fabricated by joining the posterior segments 20, 20 to the opposite ends of the anterior segment 10 as shown in FIG. 3.

Figure 9:
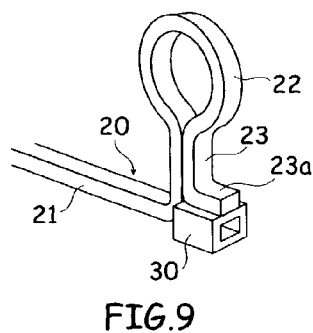
Figure 10:
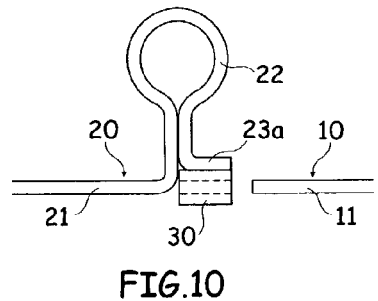

The third embodiment is a wire element with the connector 30 that is provided in advance on the bend 23a formed by bending the tip of the free end 23 of the posterior segment 20 horizontally, in such a way that the said connector has the same axial center as the main wire portion 21 (FIG. 9). As shown in FIG. 10, the axial center of the main wire portion 21 is arranged in alignment with the axial center of the connector 30. For this reason, both the posterior segment 20 and the anterior segment 10 can be connected on the same axial center by inserting one end of the anterior segment 10 into the connector 30 and crimping with pliers or the like.

Figure 11:
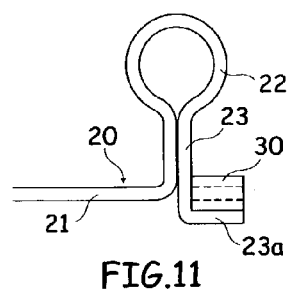
Figure 12:
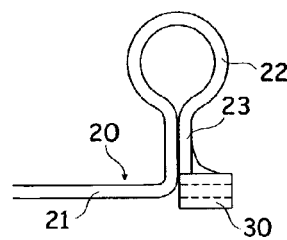

The third embodiment may be a configuration as shown in FIG. 11. As a modification of this embodiment, the connector 30 may be fitted to the free end 23 by soldering or the like in such a way that it has the same axial center as the main wire portion 21, without providing the bend 23a on the posterior segment (FIG. 12).

Figure 23:
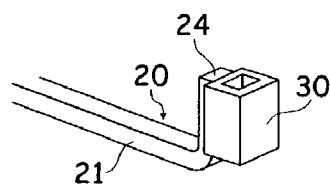

The fourth embodiment is a wire element with the connector 30 that is provided in advance on the bend 24 formed by bending one end of the posterior segment 20 at a right angle (FIG. 23). The said connector 30 provided on the bend 24 in such a way that the main wire portions 11, 21 of the anterior and posterior segments have the same axial center simply by inserting the connection end 12 of the anterior segment 10 described as the first embodiment.

Figure 24:
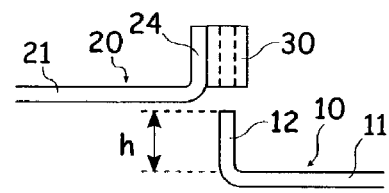

Therefore, the main wire portions 11, 12 of the anterior segment 10 and the posterior segment 20 are connected on the same axial center by inserting and positioning the connection ends 12 of the anterior segment 10 from downward into the connector 30 of the posterior segment 20 and then by crimping the above connector 30 with pliers or the like (FIG. 24).

Figure 25:
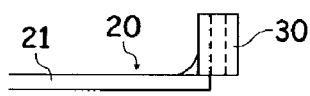
Figure 26:
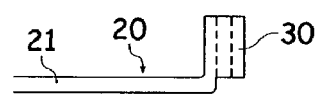

The fourth embodiment may be a configuration in which the connector 30 is secured to a straight end of the posterior segment 20 by soldering in such a way that the axial centers of both cross at a right angle (FIG. 25). In addition, a join may be provided on the posterior segment by using one-piece molding technique in such a way that the axial centers of both cross at a right angle (FIG. 26).

Figure 27:
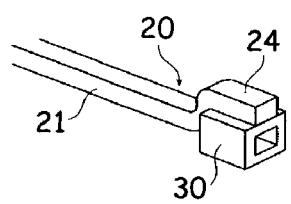
Figure 28:
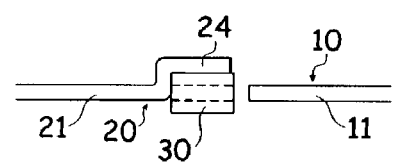

The fifth embodiment is a wire element with the connector 30 that is provided on the bend 24 formed by bending one end of the posterior segment 20 at a right angle and then in the horizontal direction in such a way that the connector 30 has the same axial center as the main wire portion 21 of the posterior segment (FIG. 27). As shown in FIG. 28, the main wire portion 21 and the connector 30 are arranged on the same axial center. For this reason, both can be connected on the same axial center by inserting one end of the anterior segment 10 into the connector 30 and then crimping with pliers or the like.

Figure 29:
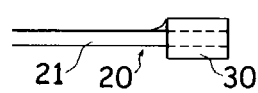
Figure 30:
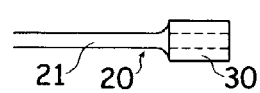

The fifth embodiment may be a configuration in which the connector 30 is secured to a straight end of the posterior segment 20 by soldering in such a way that the axial centers of both agree with each other (FIG. 29). In addition, a join may be provided to the posterior segment by using one-piece molding technique in such a way that the axial centers of both agree with each other (FIG. 30).

Figure 31:
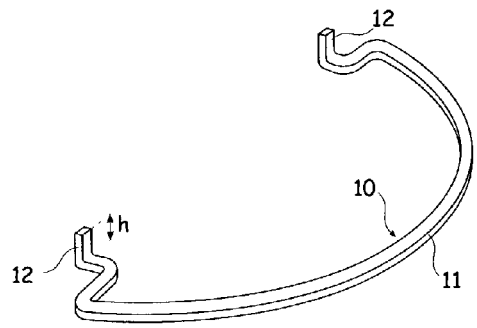

The sixth embodiment of the present invention has the anterior segment 10, as shown in FIG. 31, which is provided with connection ends 12 formed by bending at a right angle the immediate distal areas of the canine and premolar inset which is formed by bending the opposite ends of the arched main wire portion 11 in the inner direction of the arch. This is a wire element used as the anterior segment for an archwire that is used for lingually positioned orthodontic brackets. The above connection ends 12 have a height (h) that is enough to allow them to go and get locked into the connectors 30 of the posterior segment.

Figure 32:
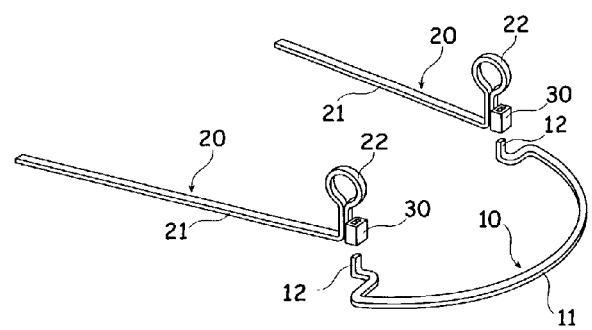

As an example of the sixth embodiment of the present invention, an archwire that is used for lingually positioned orthodontic brackets and loops can be fabricated by arranging and joining the posterior segments 20, 20 described as the second embodiment of the present invention to the opposite ends of the anterior segment 10 (FIG. 32). It is also possible to join with the fourth embodiment.

Figure 33:
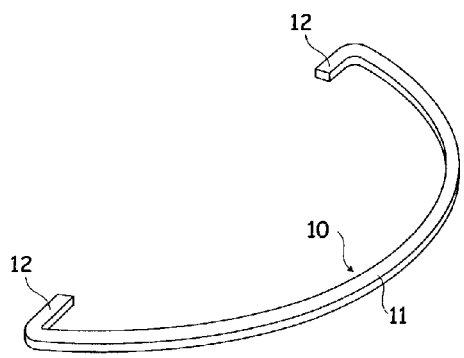

The anterior segment 10 of the seventh embodiment has connection ends 12 which are formed by bending the opposite ends of its arched main wire portion in the inner direction of the arch and double as a canine and premolar inset. This is also a wire element used as an anterior segment for the archwire that is used for lingually positioned orthodontic brackets (FIG. 33).

Figure 34:
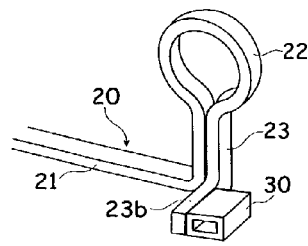

The eighth embodiment, shown in FIG. 34, is a wire element with loop used as a posterior segment for the archwire that is used for lingually positioned orthodontic brackets.

Figure 35:
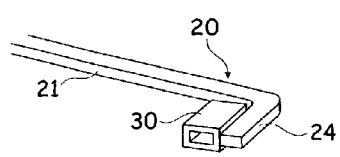

The ninth embodiment, shown in FIG. 35, is a wire element used as a posterior segment for the archwire that is used for lingually positioned orthodontic brackets.

The connector 30 provided on the posterior segment 20 of the eighth and ninth embodiments is arranged in such a way that its axial center agrees with the direction of the canine and premolar inset when the segment is used for the archwire that is used for lingually positioned orthodontic brackets.

However, in the eighth and ninth embodiments, the connector 30 may be provided directly on the free end 23 by soldering or the like without providing the bends 23b, 24 formed by bending one end of the wire.

Figure 36:
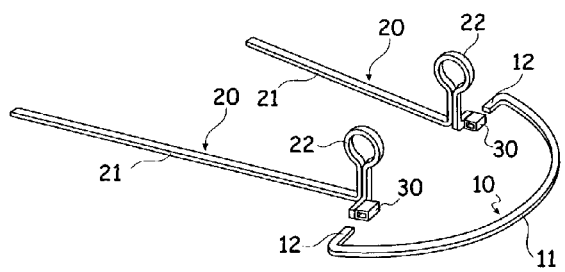

As shown in FIG. 36, an archwire that is used for lingually positioned orthodontic brackets and loops can be fabricated by arranging and joining the posterior segments 20, 20 described as the eighth embodiment of the present invention, to the opposite ends of the anterior segment of the seventh embodiment of the present invention. The seventh embodiment and the ninth embodiment can also be joined together.

In addition, the wire element of the said third embodiment or the fifth embodiment can be connected to an area corresponding to the molar site of preformed archwires that is used for lingually positioned orthodontic brackets conventionally supplied or those of your own making.

Figure 37:
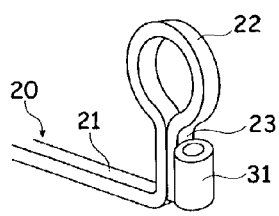

The connector 30 (FIG. 2) of the present invention may not be limited to the hollow box shape with rectangular section shown in each of the said second, third, fourth, fifth, eight, and ninth embodiments. For example, it may be a cylindrical connector 31 (FIG. 37). The connector 31 has the advantage that the wire will fit in the connector more snuggly than that of the embodiment shown in FIG. 2, if the wire element with round section is used as the mating wire for the connector 31.

Figure 38:
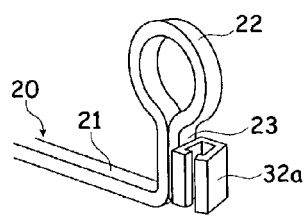
Figure 39:
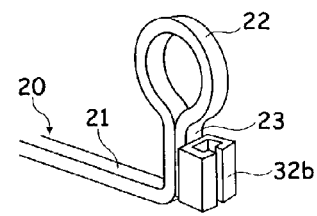

In addition, the connector may show a configuration 32a (FIG. 38) or 32b (FIG. 39) with one of the side walls cut open. Such an embodiment allows easy insertion of each end of the anterior segment into the connector.

Figure 40:
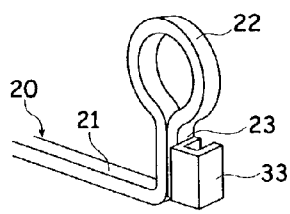

Furthermore, the connector may show a configuration 33 with one of the side walls cut away to create a plane, channel section (FIG. 40). In this embodiment, the connector 33 has the advantage that the side wall does not project sideways so that the connector may not interfere with the rotation wing of the bracket.

Figure 41:
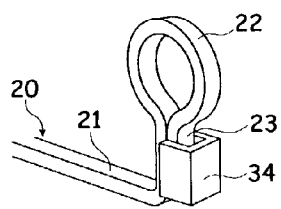
Figure 42:
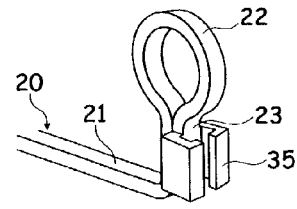

FIGS. 41 and 42 show preferred embodiments of the case where a join is provided on one end of a wire using one-piece molding technique. Such embodiments offer the advantage that the thickness of the join in the connecting direction can be reduced so that the connection of a wire element requires less space.

Figure 43:
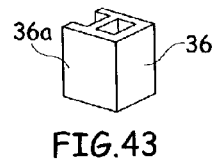
Figure 44:
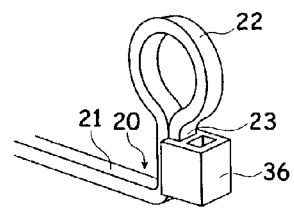

The connectors involved in the present invention, in addition to those mentioned above, may show a configuration 36 in which both-side projections 36a used for fitting are extended in parallel as shown in FIG. 43. This connector 36 allows easy positioning of the connector to the wire by using the said fitting projection 36a, thus improving the accuracy in attaching the connector to the wire. In addition, the connector 36 has the advantage that the contact area with the wire will also be increased to secure the connector more firmly (FIG. 44). Furthermore, the connector can also be provided on the wire by crimping the fitting projection 36a.

Figure 45:
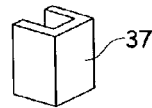
Figure 46:
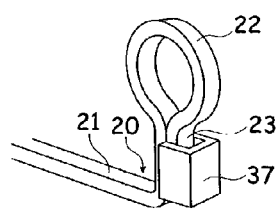

In addition, the connector may show a configuration 37 with a plane, channel section in which one end of the wire is clamped by both sides, as shown in FIG. 45. The connector 37 does not have any partition wall unlike the, said connector 36, thus leading to savings in material as well as making it easy to fabricate the connector itself. This embodiment offers the advantage that the thickness of the join in the connecting direction can be reduced so that the connection of a wire element requires less space (FIG. 46).

Figure 47:
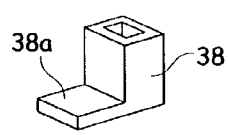
Figure 49:
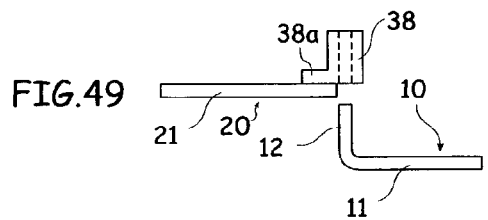
Figure 50:
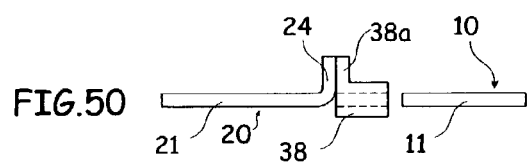
Figure 51:
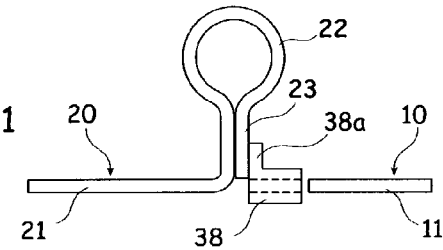

The connector of the present invention may show a configuration 38 with a fitting projection 38a as shown in FIG. 47. The use of such a connector makes it possible to fabricate wire elements as shown in FIGS. 49, 50 and 51.

Figure 52:
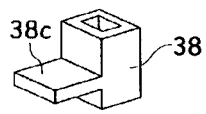
Figure 54:
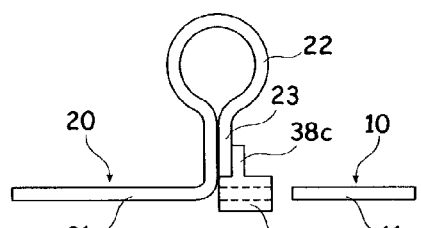

As one modification of this embodiment, there is a connector 38 with a fitting projection 38c provided at a position displaced by the thickness of a wire as shown in FIG. 52. This modification makes it easy and accurate to locate the connector 38 against the said free end 23. In addition, it has an advantage over the embodiment shown in FIG. 47 in that the connection of a wire element requires less space (FIG. 54).

Figure 55:
Figure 57:
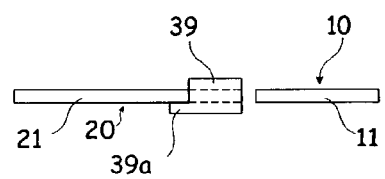

The connectors involved in the present invention may offer a configuration 39 with a fitting projection 39a as shown in FIG. 55. The use of such a connector has the advantage that the connector can be positioned through the fitting projection 39a, thus making it easy and accurate to attach the connector as well as increasing the fitting area, thus resulting in an increased strength of installation. FIG. 57 shows an example of the application of this connector.

The use of the said connector with a fitting projection makes it easy to join a wire with the connector by welding or the like.

Figure 48:
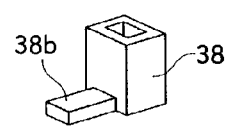
Figure 53:
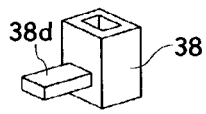
Figure 56:
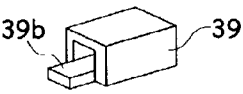

The fitting projection of the connector is not limited to a wide type (38a in FIG. 47, 38c in FIG. 52, 39a in FIG. 55), but may be a narrow type (38b in FIG. 48, 38d in FIG. 53, 39b in FIG. 56).

The wire element 10 described as the first, sixth and seventh embodiments of the present invention may be selected to suit a required size from among standard products with the main wire portion 11 and connection ends 12 preformed in advance, but connection ends 12 can be formed by the dentist himself at arbitrary positions of a preformed archwire contoured to the dental arch in advance or a wire contoured to an arch using an arch former (orthodontic appliance for bending wire elements) at the chairside.

When the dentist prepares connection ends himself, he bends one end of a wire element at the position he wants to prepare, toward the dental root and cuts the wire using a wire cutting tool to prepare a connection end 12 with a height of h. At this time, connection ends 12 can be easily cut to a height of h if the wire cutting tool 40 of the present invention shown in FIG. 58 is used.

The said wire cutting tool 40 consists of the left and right cutting dies 41 and 42 which rotate on the fulcrum 43, respectively, with the heights of the cutting edge 44 and the cutting edge receiver 45 being the same h (FIG. 59). This, for example, makes it easy to create a connection end 12 to a height of h simply by cutting with this cutting tool, with the main wire portion 11 whose opposite ends are bent aligned with the bottom surface of the cutting edge 44 of the left cutting die 41 (FIGS. 59, 60).

If the dentist is left-handed and wants to cut from an opposite direction, he can position the main wire portion 11 along the bottom surface of the cutting edge receiver 45 of the right cutting die 42 before cutting the wire. Therefore, the said wire cutting tool carries the advantage of convenience, because connection ends 12 with a height of h can be easily prepared by using the right-hand or left-hand cutting edge 44 and cutting edge receiver 45 properly.

This wire cutting tool can also be used for preparing connection ends 25 (FIG. 21) on the posterior segment which will be described later.

Archwires consisting of multiple wire elements, such as the one shown in FIG. 4, can also be supplied as a preformed item by properly combining the wire elements described as the above embodiments of the present invention.

In addition, as shown in FIG. 61, an archwire consisting of multiple wire elements can be fabricated by bundling and joining both the connection end 12 of the wire element described as the first embodiment and the connection end 25 formed by bending one end of a wire element serving as the posterior segment, using the connector 70 with an inner diameter the size of two wires. As one of the modifications of this, as shown in FIG. 62, the connection ends formed by bending two ends of the anterior and posterior segments toward the inner side of the archwire, ma be bundled using another connector 71 with an inner diameter the size of two wires. FIG. 63 shows a view of the wire join looking from the arrow Y in FIGS. 61 and 62.

Furthermore, as shown in FIG. 64, an archwire consisting of multiple wire elements can also be fabricated by lapping the connection end 25 formed by bending one end of either the anterior or the posterior segment over one end of the other, and as shown in FIG. 65 by bundling and joining them using the connector 70 with an inner diameter the size of two wires.

As one of the modifications of this, as shown in FIG. 66, connection ends 12, 25 formed by bending ends of the anterior and posterior segments may be bundled and joined using the connector 70 with an inner diameter the size of two wires, as shown in FIG. 67.

The connection ends of the anterior and posterior segments may be bundled and joined by soldering, bonding or welding, in addition to bundling with the connector.

In addition, the connectors 70, 71 with an inner diameter the size of two wires can be used for fabricating the wire element described as the fourth embodiment (FIG. 68), the wire element described as the fifth embodiment (FIG. 69), and the wire element described as the ninth embodiment (FIG. 70).

The cross section of wires involved in the present invention may be round or rectangular, but not limited in particular. Besides, the material of wires is not especially specified and can be freely selected from among stainless steel, cobalt-chrome alloy, titanium alloy, resin, and composite materials containing fiber glass and others. In addition, wires may be fine, multiple strands with an appropriate cross section. The sectional area of wire elements can be appropriately selected according to the slot size of the bracket into which the wire element is inserted.

The connector involved in the present invention may be molded separately from the wire or molded into one piece with the wire.

The material of the connector is not specified, but it is desirable to use metal molded into an appropriate configuration. The configuration of the connector may be cylindrical with an inner diameter and shape which allow the mating wire to pass, or may be generally channel-shaped with part of the sides cut away. In addition, the connector may be provided with a fitting projection which attaches to the wire.

The method of attaching the connector to a wire is not especially specified and can be freely selected from among such methods as soldering, bonding, welding, mechanical linking or one-piece molding.

A connector-fitted wire element should desirably be connected to another wire element by inserting one end of the connector-free wire element into the connector of the other wire element and then by crimping the connector with pliers or the like, but the connector may be connected to the mating wire by soldering, bonding, welding or the like.

When both the anterior and the posterior segments have connection ends, respectively, and those connection ends are to be joined, they may be done so by soldering, bonding, welding or the like in addition to bundling with the connector.

In the posterior segment of the present invention, the main wire portion 21 of the segment may be mildly arched as shown in FIG. 3 as necessary. If wire elements without an arch on the main wire portion 21, such as the posterior segment 20 shown in FIG. 2, are prepared, the number of types of loop-fitted wire elements that need to be stocked will be reduced, thus allowing easy inventory control. In contrast, if the posterior segment 20 given an arch in advance on the main wire portion 21 as shown in FIG. 3 is prepared, it will be convenient because it can be used without any additional work.

In the posterior segment with loops of the present invention (such as those of the second, third and eighth embodiments), the loops 22 formed on the posterior segment 20 are not limited to those shown in FIGS. 2 to 12 and may be any of a variety of shapes as shown in FIGS. 13 to 20.

If an archwire is prepared by combining wire elements of the present invention, no misalignment of the axial center does not occur between the main wire portions of the wire elements so that the use of brackets which allow for misalignment of the axial center between the wires or the adjustment of the archwire required by the conventional art is no longer necessary, thus making it possible to shorten the treatment time at the chairside.

The wire elements (those of the second and fourth embodiments, and others) forming the posterior segment equipped with the connector 30 which stands vertically against the axial center of the main wire portion 21 of the wire do not require large space for connecting the anterior segment 10 to the posterior segment 20. As a result, it is possible to create a loop at a narrow area between the brackets. In addition, they have the advantage that the connection end 12 of the anterior segment is engaged in the connector 30 and thus it is hard to come off.

The connection of the seventh embodiment and the eighth embodiment, and the connection of the seventh embodiment and the ninth embodiment have the advantage that they are hard to come off against the tensile stress in the mesiodistal direction.

When the wire element described as the fourth embodiment is used or when both the anterior segment and the posterior segment have connection ends and they are joined together (FIGS. 61, 62), the junction projects vertically from the main wire portion of the archwire, offering convenience of serving as a hook when using intermaxillary elastics or the like.

When the connector 30 of the wire elements (third and fifth embodiments) on which the connector 30 is arranged in such a way that its axial center agrees with the axial center of the main wire portion 21 is fitted to the anterior segment 10, it is generally sufficient if the connector 30 is just long enough to secure only one end of the anterior segment 10. For this reason, this structure has the advantage over the conventional art which secures the ends of the two butted mating wire elements in that only a half of the length of the conventional connector is required and thus it can also be applied for narrow bracket spacing.

If the posterior segments of these types are used with an anterior segment made of too flexible a material that is hard to shape at the chairside, such as titanium alloy wire, it is especially convenient because the anterior segment does not need to have connection ends, thus shortening the treatment time.

If the wire element 10 (the first, sixth and seventh embodiments) forming the anterior segment of the present invention is made of a wire material that can be easily bent at the chairside, the dentist may prepare the anterior segment himself. For example, using a wire appropriately arched by the dentist or a preformed archwire, the dentist can prepare the connection end 12 by bending one end of the wire at an arbitrary position at a right angle and cutting the bend to a height of h. This way, since the connection end 12 of the anterior segment can easily be prepared at an arbitrary position, the anterior segment and the posterior segment can easily be connected at an arbitrary position without requiring long connection space, so that the prepared archwire has a wide application range. In addition, unlike the conventional art, there is no need to stock a lot of wires with different loop spacings, thus allowing easy inventory control.

If the arch of the main wire portion 11 and the connection ends 12 of the anterior segment are prepared in advance, it is convenient because there is no need to bend the wire at the chairside. In particular, if the anterior segment 10 is made of too flexible a material that cannot easily be shaped at the chairside, such as titanium alloy, the treatment time can be shortened by arching the main wire portion 11 and preparing the connection end 12 in advance.

The present invention makes it possible to freely select the physical properties and configuration of the wires and the shape and position of the loop. In addition, as shown in FIGS. 21 and 22, multiple loops can be connected in sequence or loops of different types can also be combined. FIG. 21 shows a method of connecting multiple loops using the second embodiment as an example. In this case, the connection with the wire element of another posterior segment can be achieved by forming the connection end 25 by bending the wire end opposite the connection end of the posterior segment 20. Furthermore, in FIG. 22, a method of connecting multiple loops of different types is shown using the third embodiment as an example. This way, versatile archwires that cope with a variety of conditions can be prepared by combining a few types of wire elements having a single loop, thus allowing easy inventory control.

In the present invention, the posterior segment 20 has the connector 30 provided in advance to connect to the anterior segment 10. It saves the trouble of preparing the connector 30 separately from the posterior segment 20 and installing the connector 30 to the posterior segment 20 when connecting the posterior segment to the anterior segment.

Furthermore, the connector 30 itself is small and may easily be lost, but since it is provided on the posterior segment 20 in advance, its loss can be prevented.

The archwire manufacturing method of the present invention allows trial fitting of the archwire, pointing the wire end on which the connector 30 is provided toward the distal side of the patient when directly measuring the length of the main wire portion 21 required as the posterior segment in the oral cavity of the patient. Therefore, it has the advantage that the patient's oral mucosa may not be damaged by one end of the wire element, unlike the conventional art. This is especially useful when preparing an archwire with loops.

When the formation of loops on an archwire is needed, an archwire with a desired configuration can be obtained simply by selecting and connecting a posterior segment 20 with a loop of necessary configuration. Therefore, there is no need to prepare loops at the chairside so that the treatment time can be remarkably reduced. In addition, since there are no variations in the dimensional accuracy of loops, even unskilled dentists about this procedure can prepare archwires of high accuracy.

Wires of various materials or configurations can easily be joined to the archwire by preparing posterior segments without loop. In addition, it is also possible to prepare an arbitrary loop on the said wire element and join the said wire element to another wire.

The method of preparing connection ends on both the anterior segment and the posterior segment, respectively, and joining them to each other increases the join area of the wires, compared with the conventional method of butt-joining the respective ends of two wires, because the connection ends formed by bending are joined together. This provides strong linkage between the two wire elements.

What I claim as my invention is:

1. An orthodontic archwire comprising an anterior segment and two posterior segments connected to both ends of the anterior segment,
    the anterior segment being composed of a first archwire element, the first archwire element having an arched main wire portion, and two connection ends formed at each end of the arched main wire portion and bent at right angles to the arched main wire portion,
    each of the posterior segments being composed of a second archwire element, the second archwire element having a main wire portion, a loop formed at one end of the main wire portion, a leg formed at an free end of the loop perpendicular to the main wire portion, and a connector provided on the leg and parallel to the leg, into which the connecting end of the first archwire element is inserted and locked coupling the anterior segment and the posterior segments such that the central axis of each segment is mated and co-linear.

2. An orthodontic archwire comprising an anterior segment and two posterior segments connected to both ends of the anterior segment,
    the anterior segment being composed of a first archwire element, the first archwire element having an arched main wire portion, and two connection ends formed at each end of the arched main wire portion and bent at right angles to the arched main wire portion, each of the posterior segments being composed of a plurality of second archwire elements connected in series, the second archwire elements each having a main wire portion, a loop formed at one end of the main wire portion, a leg formed at an free end of the loop and perpendicular to the main wire portion, a connection end formed at the other end of the main wire portion and bent at right angles to the main wire portion, and a connector provided on the leg and parallel to the leg, into which the connection end of the first archwire element or the adjacent second archwire element is inserted and locked coupling the anterior segment and the posterior segments such that the central axis of each segment is mated and co-linear.

* * * * *